United States Patent [19]

Crandell

[11] 4,225,582
[45] Sep. 30, 1980

[54] VACCINE FOR EQUINE RHINOPNEUMONITIS

[75] Inventor: Robert A. Crandell, Champaign, Ill.

[73] Assignee: The University of Illinois Foundation, Urbana, Ill.

[21] Appl. No.: 18,458

[22] Filed: Mar. 8, 1979

[51] Int. Cl.³ .............................................. A61K 39/12
[52] U.S. Cl. ..................................................... 424/89
[58] Field of Search .................................... 424/85–93

[56] References Cited

U.S. PATENT DOCUMENTS

| | | | |
|---|---|---|---|
| 2,934,473 | 4/1960 | York et al. | 424/89 |
| 2,941,925 | 6/1960 | York et al. | 424/89 |
| 3,048,524 | 8/1962 | Bass | 424/89 |
| 3,057,783 | 10/1962 | Cabasso | 424/89 |
| 3,256,152 | 6/1966 | Lampson | 424/85 |
| 3,465,077 | 9/1969 | Baker | 424/89 |
| 3,518,347 | 6/1970 | Pavilanis et al. | 424/89 |
| 3,541,206 | 11/1970 | Hall | 424/89 |
| 3,674,864 | 7/1972 | Angelucci | 424/90 |
| 3,725,542 | 4/1973 | Mayr | 424/89 |
| 3,876,764 | 4/1975 | Straub | 424/89 |
| 3,907,986 | 9/1975 | Zygraich et al. | 424/89 |
| 3,927,208 | 12/1975 | Zygraich et al. | 424/89 |
| 3,927,209 | 12/1975 | Straub | 424/89 |
| 3,962,424 | 6/1976 | Zygraich et al. | 424/89 |
| 4,017,359 | 4/1977 | Straub | 195/1.3 |
| 4,083,958 | 4/1978 | Bryans | 424/89 |
| 4,110,433 | 8/1978 | Purdy | 424/89 |
| 4,132,775 | 1/1979 | Volenec et al. | 424/89 |

OTHER PUBLICATIONS

Buxton et al., Animal Microbiology, vol. 2, Blackwell Scientific Publications Ltd., Oxford, U.K. (1977), pp. 406A–427, "The Classification of Anival Viruses".

Crandell, R. A., et al., Theriogenology 6(1): 1–19 Jul. 1976, The Isolation and Characterization of a New Bovine Herpesvirus Associated with Abortion (Cattle).

Crandell, R. A., et al., Can. J. Comp. Med. 43(1): 94–97 (1979) A Comparative Study of Bovine Herpesvirus 1247 and Equine Herpesvirus 1 in Ponies.

Carmichael et al., Vet. Bull. 32(9) 603 of Proc. 65th Ann. Mtg. U.S. Livestock Sanitary Assn. (1962), pp. 384–388, The Relationship of Infectious Bovine Rhinotracheitis Virus to Equine Rhinopneumonitis Virus.

Fulton Vet. Bull. 46:5633 (1976) of Dissertation Abstracts Int. (1976) 36B(10):4890 (No. 76–7488) In Vitro Interferon Production in Bovine Tissues Induced with Infectious Bovine Rhinotracheitis.

Straub et al., Vet. Bull. 46:6975 (1976) of Zent. F. Vet. 1976, 23B(5/6):470–482, Local Production of Interferon in Cattle After Intranasal Infection with Avirulent IBR-/IPV Virus.

Primary Examiner—Shep K. Rose
Attorney, Agent, or Firm—Jerome M. Teplitz; A. Sidney Alpert; David N. Koffsky

[57] ABSTRACT

Live Bovine Herpesvirus A.T.C.C. VR-2003 is employed in vaccination of horses to confer immunity to infection by Equid Herpesvirus Type 1.

5 Claims, No Drawings

VACCINE FOR EQUINE RHINOPNEUMONITIS

BACKGROUND

The present invention relates generally to novel immunological materials and methods, and more particularly to treatment of horses to confer immunity to infection by Equid Herpesvirus Type 1.

Equine rhinopneumonitis is an infectious disease of horses caused by a viral strain known as Equid Herpesvirus Type 1 (hereafter, "EHV 1"). The disease state is variously characterized by upper respiratory infection, by abortion in pregnant mares, and by neuro-musclar symptoms such as ataxia and paresis. While EHV 1 is known to produce abortion in hamsters, calves are reported to be refractory to infection with this virus.

Commercial vaccines comprising hamster-adapted and tissue cultured live EHV 1 virus have been generally inadequate in controlling the spread of the disease. More particularly, administration of prior art vaccines has frequently been accompanied by incidences of abortion in mares vaccinated during pregnancy and by infection of contact animals by vaccine virus shed nasally after vaccination. As a result, vaccination of pregnant mares is avoided as is vaccination of horses expected to come in contact with unvaccinated mares. There therefore exists a need for vaccine materials and methods which confer immunity to infection by EHV 1 but which are safe when administered to pregnant mares and which do not give rise to shedding of infective vaccine virus after vaccination.

This invention has its background in part in the inventor's discovery and isolation of a herpesvirus from the lung of an aborted Hereford fetus. The isolation of this herpesvirus is one of two known isolations from the bovine species. The specific virus isolated by the inventor was shown by him to possess physical properties common to those of the herpesviruses, e.g., typical herpesvirus morphology as confirmed by electron microscopic studies. The virus was found to be sensitive to chloroform and its replication was inhibited by 5-iododeoxyuridine. Initial serum neutralization tests using diluted typing sera specific for EHV 1 showed the newly-isolated viral strain (designated "Bovine Herpesvirus No. 1247") to be distinct from, inter alia, the equine herpesvirus responsible for equine rhinopneumonitis. See, generally, Crandell, et al, "Theriogenology", 6, pp. 1–19, (1976). Subsequent independent studies of samples of the new virus showed, however, the existence of serologic relation with other viruses, and specifically with EHV 1. See, Kanitz, et al, "Proceedings, 19th Meeting American Association of Veterinary Laboratory Diagnosticians," pp. 1–12 (Nov. 1976) and Smith, "Proceedings, 80th, Meeting, U.S. Animal Health Association," pp. 149–158, (1976).

In a comparative study of Bovine Herpesvirus No. 1247 and EHV 1, the inventor ascertained that the bovine virus was in fact nasally infective in horses, generating a mild rhinitis and increase in rectal temperature. The inoculated ponies developed measurable serum neutralizing antibodies to the vaccine virus as well as to the equine virus (EHV 1).

BRIEF SUMMARY

According to the present invention vaccines are prepared which comprised Bovine Herpesvirus A.T.C.C. No. VR-2003 in dosage amounts of from about $10^3$ to about $10^6$ $TCID_{50}$ dispersed in an immunologically acceptable carrier. Mutant forms of A.T.C.C. No. VR-2003 prepared, e.g., by propagation at reduced temperatures and/or in the presence of mutagenic chemicals, are also expected to be useful. Vaccines so prepared are administered to horses intranasally or parenterally (intramuscularly or subcutaneously) and confer immunity to infection against EHV 1.

Horses vaccinated according to the methods of the present invention develop enhanced antibody titers to EHV 1 and post-vaccination challenge with EHV 1 gives rise to substantially diminished symptoms of infection. Vaccination of pregnant mares does not give rise to abortion. Finally, vaccine virus is not shed by vaccinated animals, therefore it does not appear to be a problem for contact animals.

DETAILED DESCRIPTION

The Bovine Herpesvirus strain employed in the practice of the present invention possesses biochemical and biophysical properties common to members of the herpesvirus group. Its replication is inhibited by 5-iododeoxyuridine, indicating that its essential nucleic acid is DNA. The virus is sensitive to chloroform treatment and is heat labile. Virus particle morphology is similar to the other herpesviruses. [See, e.g., Wilner, "A Classification of the Major Groups of Human and Other Animal Viruses," Ch. 10, p. 103 (Burgess Pub. Co., Minneapolis, Minn. 4th Ed. 1969].

The virus has been deposited by the inventor and is available from American Type Culture Collection, 12301 Parklawn, Rockville, Md. 20852 under the designation A.T.C.C. VR-2003. The deposited viral strain is the result of sixteen serial passages of the original bovine isolate in primary bovine embryonic kidney (BEK) cells [Flow Laboratories] maintained on medium MEM [Grand Island Biological Company] plus 2% bovine fetal serum. The culture medium also contained 200 units of penicillin, 200 mg of streptomycin, and 2.5 mg of amphotericin B per ml.

The following example illustrates the effectiveness of Bovine Herpesvirus A.T.C.C. VR-2003 a live viral component of a vaccine to confer immunity to infection by EHV 1.

EXAMPLE 1

Animals. Six shetland mare ponies in differing stages of gestation were employed.

Cell Cultures. Propagation of viral strains was carried out in equine embryonic kidney (EEK) cells in third and sixth subcultures grown in tubes and flasks with Eagle's minimum essential medium (MEM). Pig kidney (PK-15) cells for use in serum neutralization tests were grown in MEM with nonessential amino acids, glutamine, 0.5% lactalbumin hydrolysate, and 10% fetal bovine serum. All culture media additionally included 200 units of penicillin, 200 μg of streptomycin, and 2.5 μg of Amphotericin B per ml.

Sample collection. Nasal swabs for virus isolation were obtained by streaking the nasal septum with a cotton tipped applicator. Swabs were stored in 1 ml MEM medium at −70° C. until testing. Serum samples for serological tests were collected at time intervals indicated infra.

Virus Isolations. BEK and EEK cell cultures were inoculated with 0.2 ml of MEM fluid containing nasal specimens and observed daily for cytopathic changes characterized by syncytial formations with destruction of the cell monolayer.

Serum-Virus Neutralization Tests. Reciprocal serum-virus neutralization tests were performed with EHV 1 by microtiter methods unless otherwise indicated. Equal amounts of serum and virus were mixed with 200 to 300 $TCID_{50}$ doses of virus and were incubated at 37° C. for one hour before adding PK-15 cells. Serum titers are expressed as the reciprocal of the final serum dilution in which cytopathic changes were absent after 5 days.

Vaccines. Bovine Herpesvirus A.T.C.C. VR-2003 was propagated in quantity in the second subculture of EEK cells described above. The virus inoculated cultures were incubated for 4 days at 36° C. Following one freeze and thaw cycle, the virus suspension was clarified by low speed centrifugation. The vaccine (virus) was dispensed into vaccine bottles and stored at $-70°$ C. until used. The EHV 1 employed was originally isolated from the liver of an aborted foal and was propagated in quantity after five serial passages in EEK cells.

Procedure. Ponies No. 1 through 5 were inoculated subcutaneously with one 10 ml. dose containing $10^{5.6}$ $TCID_{50}$ of Bovine Herpesvirus A.T.C.C. VR-2003 in MEM fluid. Pony No. 6 served as a contact control and was inoculated with 10 ml of normal culture medium (MEM) in two sites. The EHV 1challenge virus was administered to ponies No. 2 through 6, 14 days after foaling of the last-to-foal mare. The challenge virus was inoculated intranasally in a 5 ml. dose containing $10^{5.7}$ $TCID_{50}$ virus. Sera was collected and subjected to serum neutralization testing before vaccination, at 14, 21, and 192 or 208 days after vaccination, and 21 days after the EHV 1 challenge inoculation. Virus isolations from nasal passages were obtained on the day of EHV 1 challenge and on each of the eight days following challenge.

Results. Table 1 below provides data concerning the experimental animals in terms of age, day of gestation at the time of vaccination, and days after vaccination when mares foaled. Significantly, there was no incidence of abortion in any of the vaccinated ponies, nor was there abortion in the control pony.

TABLE 1

| Pony No. | Age (yrs.) | Day of Gestation at Vaccination | Days after Vaccination Mare Foaled |
|---|---|---|---|
| 1 | 12 | 303 | 40 |
| 2 | 7 | 227 | 116 |
| 3 | 14 | 319 | 24 |
| 4 | 3 | 309 | 34 |
| 5 | 4 | 319 | 24 |
| 6* | 14 | 149 | 194 |

*Unvaccinated Control

Table 2 below provides data concerning serum neutralization titers to EHV 1 by microtiter method, reported as the reciprocal of endpoint dilution. Bracketed values are those obtained by standard tube methods, without complement added, using 0.2 ml inoculum. All but the control animal showed significant increases in EHV 1 antibody titers after vaccination with Bovine Herpesvirus A.T.C.C. VR-2003.

TABLE 2

Serum Neutralization Titer

| Pony No. | Pre-Vaccination | Post-Vaccination Days | | | Post-Challenge Days |
|---|---|---|---|---|---|
| | | 14 | 21 | 208 | 21 |
| 1 | 16 [22] | 64 | 64 [710] | (1) | — |
| 2 | 32 [26] | NT(2) | 128 [356] | 64(3) | 128 |
| 3 | 64 [14] | NT | 128 [296] | 64(3) | 128 |
| 4 | 4 [10] | 64 | 128 [1002] | 128 | 256 |
| 5 | 4 [12] | 64 | 64 [710] | 64 | 512 |
| 6(control) | 4 [22] | 8 | 4 [22] | 16 | 256 |

(1)Pony No. 1 was sacrificed because of injury.
(2)Not Tested.
(3)Titers are 192 days post-vaccination.

Table 3 below provides data concerning isolation of virus shed by the ponies after EHV 1 challenge. Vaccination with Bovine Herpesvirus A.T.C.C. VR-2003 diminished virus shedding to 1 day indicating that only residual virus (the inoculum) was recovered.

TABLE 3

Virus Isolation

| Pony No. | Days Post-Challenge | | | | | | | | |
|---|---|---|---|---|---|---|---|---|---|
| | 0 | 1 | 2 | 3 | 4 | 5 | 6 | 7 | 8 |
| 2 | — | + | — | — | — | — | — | — | — |
| 3 | — | + | — | — | — | — | — | — | — |
| 4 | — | + | — | — | — | — | — | — | — |
| 5 | — | + | — | — | — | — | — | — | — |
| 6 | — | + | + | + | — | — | — | — | — |

Suitable vaccines prepared according to the present invention contain dosage amounts of from about $10^3$ to about $10^6$ $TCID_{50}$ of the live virus and preferably about $10^4$ to about $10^5$. Suitable immunologically acceptable carriers for the virus include cell culture fluid and a stabilizer. Administration of the vaccine according to the methods of the invention is preferably by the intranasal route and parenteral routes including subcutaneous and intramuscular.

As indicated in the foregoing example, it is preferred that Bovine Herpesvirus A.T.C.C. VR-2003 be propagated in cell cultures of equine origin prior to vaccine preparation. This is due to the observed enhanced replication of the virus in cells of equine origin as opposed to bovine cell cultures in which it is maintained.

It is within the contemplation of the present invention that Bovine Herpesvirus A.T.C.C. VR-2003 may be subjected to multiple serial passages in cell cultures of equine, bovine, or other species prior to use in vaccine preparations. It is also contemplated that mutant forms of A.T.C.C. VR-2003 will be useful in practice of the invention. Modifying procedures including propogation of the virus at lower temperatures and/or with mutagenic chemical treatments are expected to permit selection of more temperature-sensitive viruses suitable as vaccine strains. Such procedures are expected to decrease virulence or infectivity without substantially diminishing the antigenicity of the A.T.C.C. VR-2003 strain.

Numerous modifications and variations of the above disclosed methods and materials of the invention are expected to occur to those skilled in the art. Consequently only such limitations as appear in the appended claims should be placed on the invention.

What is claimed is:

1. A method for treatment of a horse to confer immunity to infection by Equid Herpesvirus Type 1, said method consisting of administrating a vaccine comprising an immunologically effective amount of the live Bovine Herpesvirus A.T.C.C. No. VR-2003.

2. The method of claim 1 wherein the dose of live virus administered is from about $10^3$ to about $10^6$ $TCID_{50}$.

3. The method of claim 1 wherein the mode of administration of said vaccine is intranasal.

4. The method of claim 1 wherein the mode of administration is parenteral.

5. A vaccine suitable for use in conferring upon horses immunity to infection by Equid Herpesvirus Type 1, said vaccine comprising, in unit dosage form, from about $10^3$ to about $10^6$ $TCID_{50}$ of Bovine Herpesvirus A.T.C.C. VR-2003 in combination with an immunologically acceptable carrier.

* * * * *

UNITED STATES PATENT AND TRADEMARK OFFICE
CERTIFICATE OF CORRECTION

PATENT NO. : 4,225,582
DATED : September 30, 1980
INVENTOR(S) : Robert A. Crandell It is certified that error appears in the above—identified patent and that said Letters Patent is hereby corrected as shown below:

Column 1, Line 57, after the comma, insert -- [Crandell, et al., "Canadian Journal of Comparative Medicine", 43, pp. 94-97 (1979)], --.

Signed and Sealed this

Twenty-seventh Day of January 1981

[SEAL]

Attest:

RENE D. TEGTMEYER

Attesting Officer

Acting Commissioner of Patents and Trademarks